United States Patent
Wittner et al.

(10) Patent No.: US 8,231,377 B2
(45) Date of Patent: Jul. 31, 2012

(54) APPARATUS AND METHOD FOR STRETCHING AN EXTENSIBLE SHEET MATERIAL

(75) Inventors: Manfred Wittner, Mannheim (DE); Jean-Claude Abed, Simpsonville, SC (US)

(73) Assignee: Fiberweb Corovin GmbH, Peine (DE)

( * ) Notice: Subject to any disclaimer, the term of this patent is extended or adjusted under 35 U.S.C. 154(b) by 675 days.

(21) Appl. No.: 11/669,234

(22) Filed: Jan. 31, 2007

(65) Prior Publication Data
US 2007/0212966 A1   Sep. 13, 2007

Related U.S. Application Data

(60) Provisional application No. 60/763,543, filed on Jan. 31, 2006.

(51) Int. Cl.
*B29C 43/46* (2006.01)
*B29C 55/18* (2006.01)
(52) U.S. Cl. .......... 425/365; 425/335; 425/471; 492/30
(58) Field of Classification Search .................. 425/335, 425/336, 362, 363, 367, 369, 471; 492/30; 264/280, 285, 286, 288.4; 101/6, 23
See application file for complete search history.

(56) References Cited

U.S. PATENT DOCUMENTS

| | | | |
|---|---|---|---|
| 3,555,596 A * | 1/1971 | Thieme | 425/154 |
| 3,899,805 A * | 8/1975 | McMillan | 24/584.1 |
| 4,116,892 A | 9/1978 | Schwarz | |
| 4,285,100 A | 8/1981 | Schwarz | |
| 4,323,068 A | 4/1982 | Aziz | |
| 4,368,565 A | 1/1983 | Schwarz | |
| 4,592,943 A | 6/1986 | Cancian et al. | |
| 4,603,445 A * | 8/1986 | Spann | 5/736 |
| 4,682,540 A | 7/1987 | Eastman et al. | |
| 4,759,967 A * | 7/1988 | Bauernfeind | 428/154 |
| 4,774,124 A | 9/1988 | Shimalla et al. | |

(Continued)

FOREIGN PATENT DOCUMENTS
DE   197 21 370   11/1998
(Continued)

OTHER PUBLICATIONS

International Preliminary Report on Patentability for PCT/US2007/061344 dated Apr. 24, 2008.

(Continued)

*Primary Examiner* — Richard Crispino
*Assistant Examiner* — Robert Dye
(74) *Attorney, Agent, or Firm* — Alston & Bird LLP (57) ABSTRACT

The invention provides a roll assembly including a pair of cylindrical rolls that are positioned in an opposing cooperating relation for receiving a sheet material therebetween. A plurality of projections on at least one of the rolls extending radially outward from a surface thereof and a plurality of corresponding recesses is provided on the other roll. The projections and corresponding recesses are positioned and arranged on the rolls for contacting and engaging a sheet passing between the pair of rolls. The projections each include an outermost surface portion that is positioned for contacting a discrete portion of the sheet and for entering a corresponding recess on the opposite roll. When rolls rotate about their axes, the projections engage the discrete portion of the sheet material which results in the discrete portion entering the recesses with the projections so as to stretch the sheet in multiple directions.

15 Claims, 4 Drawing Sheets

U.S. PATENT DOCUMENTS

| | | | | |
|---|---|---|---|---|
| 5,188,625 A * | 2/1993 | Van Iten et al. | | 604/383 |
| 5,356,364 A | 10/1994 | Veith et al. | | |
| 5,399,174 A | 3/1995 | Yeo et al. | | |
| 5,422,172 A | 6/1995 | Wu | | |
| 5,534,208 A * | 7/1996 | Barr et al. | | 264/160 |
| 5,592,690 A | 1/1997 | Wu | | |
| 5,861,074 A | 1/1999 | Wu | | |
| 5,897,930 A | 4/1999 | Calhoun et al. | | |
| 5,913,765 A * | 6/1999 | Burgess et al. | | 493/403 |
| 5,921,973 A | 7/1999 | Newkirk et al. | | |
| 6,173,496 B1 | 1/2001 | Makoui et al. | | |
| 6,344,102 B1 | 2/2002 | Wagner | | |
| 6,417,121 B1 | 7/2002 | Newkirk et al. | | |
| 6,417,122 B1 | 7/2002 | Newkirk et al. | | |
| 6,420,285 B1 | 7/2002 | Newkirk et al. | | |
| 6,506,698 B1 | 1/2003 | Quantrille et al. | | |
| 6,632,504 B1 | 10/2003 | Gillespie et al. | | |
| 6,878,647 B1 | 4/2005 | Rezai et al. | | |
| 7,229,681 B2 * | 6/2007 | Boegli | | 428/156 |
| 7,955,544 B2 * | 6/2011 | Contreras | | 264/284 |
| 2002/0016122 A1 | 2/2002 | Curro et al. | | |
| 2003/0085213 A1 * | 5/2003 | Burckhardt et al. | | 219/243 |

FOREIGN PATENT DOCUMENTS

| | | |
|---|---|---|
| WO | WO 93/01047 | 1/1993 |
| WO | WO 97/22742 | 6/1997 |
| WO | WO 03/000165 | 1/2003 |

OTHER PUBLICATIONS

Partial Search Report for PCT/US2007/061344 dated May 25, 2007.

Search Report and Written Opinion for PCT/US2007/061344 dated Sep. 13, 2007.

* cited by examiner

APPARATUS AND METHOD FOR STRETCHING AN EXTENSIBLE SHEET MATERIAL

CROSS REFERENCE TO RELATED APPLICATIONS

This application is related to commonly owned Provisional Application Ser. No. 60/763,543, filed Jan. 31, 2006, incorporated herein by reference in its entirety, and claims the benefit of its earlier filing date under 35 U.S.C. 119(e).

BACKGROUND OF THE INVENTION

The present invention relates generally to the stretching of sheet materials and more particularly to an apparatus and method for stretching extensible sheet materials such as nonwoven webs and laminates.

Sheet materials such as nonwoven webs, fabrics, films, and laminates are used in a wide variety of applications such as garments, disposable medical products, diapers and personal hygiene products. New products being developed for these applications have demanding performance requirements, including comfort, conformability to the body, freedom of body movement, good softness and drape, adequate tensile strength and durability and resistance to surface abrasion.

In many instances, it may be desirable to stretch the sheet material to provide improved properties such as softness, elasticity, drape, and the like. According to Sabee, U.S. Pat. Nos. 4,153,664 and 4,223,063, the softness and drapeability of nonwoven fabrics can be improved by drawing or stretching the fabric. More particularly, according to these patents the nonwoven fabrics are processed by differentially drawing or stretching the web by passing the fabric through a pair of intermeshing grooved rolls to form a pattern of drawn and undrawn areas.

For some applications, the nonwoven fabric must have elastic properties. In certain disposable diaper designs, for example, it is desired to impart elasticity to the waist and/or to the leg cuff areas. One approach to imparting elastic properties to a nonwoven fabric is with a so-called "zero-strain" stretchable laminate. A "zero-strain" stretchable laminate refers to a fabric in which at least two layers of material, one elastic and the other substantially inelastic, are secured to one another along their coextensive surfaces while in a substantially untensioned state. The fabric is subsequently subjected to mechanical stretching by "ring-rolling"—a process wherein the laminate is directed between one or more pairs of intermeshed grooved rolls. This causes the inelastic layer to be permanently elongated and gives the laminate elastic properties. Conventional ring-rolling process for mechanically stretching the sheet material are limited to stretching the sheet in the machine direction and/or in the cross-machine section direction of the sheet material. As a result, the stretched material has elastic properties along either the machine direction or the cross direction or both. However, for many materials, it would be desirable to have a material having elastic properties in more than two directions. For example, in clothing applications, to permit free movement in all directions it may be desirable to provide a material that is stretched in multiple directions and has elastic properties along multiple directions.

BRIEF SUMMARY OF THE INVENTION

The invention provides an apparatus and method that can be used to stretch a sheet material in multiple directions so that the sheet material may have multi-dimensional elastic properties. In one embodiment, the invention is directed to a roll assembly comprising a pair of cylindrical rolls that are positioned in an opposing cooperating relation for receiving a sheet material therebetween. The roll assembly includes a plurality of projections on at least one of the rolls that extending radially outward from a surface of the roll and the other roll includes a plurality of recesses that correspond to the projections. The projections and corresponding recesses are positioned and arranged on the rolls for contacting and engaging a sheet material passing between the pair of rolls. The projections each include an outermost surface portion that is positioned for contacting a discrete portion of the sheet material and for entering a corresponding recess on the opposite roll. The discrete portion of the sheet material is stretched as the projection and the discrete portion of the sheet material enter into a corresponding recess.

The recesses are located on the surface of at least one of rolls and are correspondingly arranged so as to receive a corresponding projection disposed on the opposite roll. When the rolls are rotated about their axes, the recesses successively becomes aligned opposite a corresponding projection so that the aligned projections are then able to at least partially enter into the corresponding recess. As a sheet material passes between the rolls, projections that are in contact with the sheet material each engage a discrete portion of the sheet material. This engagement causes the discrete portions of the sheet material to enter into the recesses along with the projections. As a result, these discrete portions of the sheet material entering the recess stretch and form discrete regions on the sheet that have been mechanically elongated. The discrete portions of the sheet material are stretched in multidirections and are not limited to stretching in only one or two directions.

In one embodiment, the recesses comprises free standing recesses that are unconnected to adjacent recesses. In some embodiments, the size and shape of the recesses are configured to produce stretched portions of the sheet material that are free-standing and unconnected to adjacent stretched portions. As a result, isolated stretched region of the sheet material can be produced that have island-like shapes. The resulting island-like stretched portions are separated from one another by substantially unstretched portions of the sheet material. The resulting island like stretched portion permits the sheet material to have multi-directional stretch properties.

In one embodiment, the amount of stretching that occurs within each discrete stretched portion can be controlled by adjusting the distance between the pair of rolls and the depth of penetration of the projections into the corresponding recesses. The density and distribution of the recesses and projections can also be selected to produce a sheet material having a desired degree of stretching.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
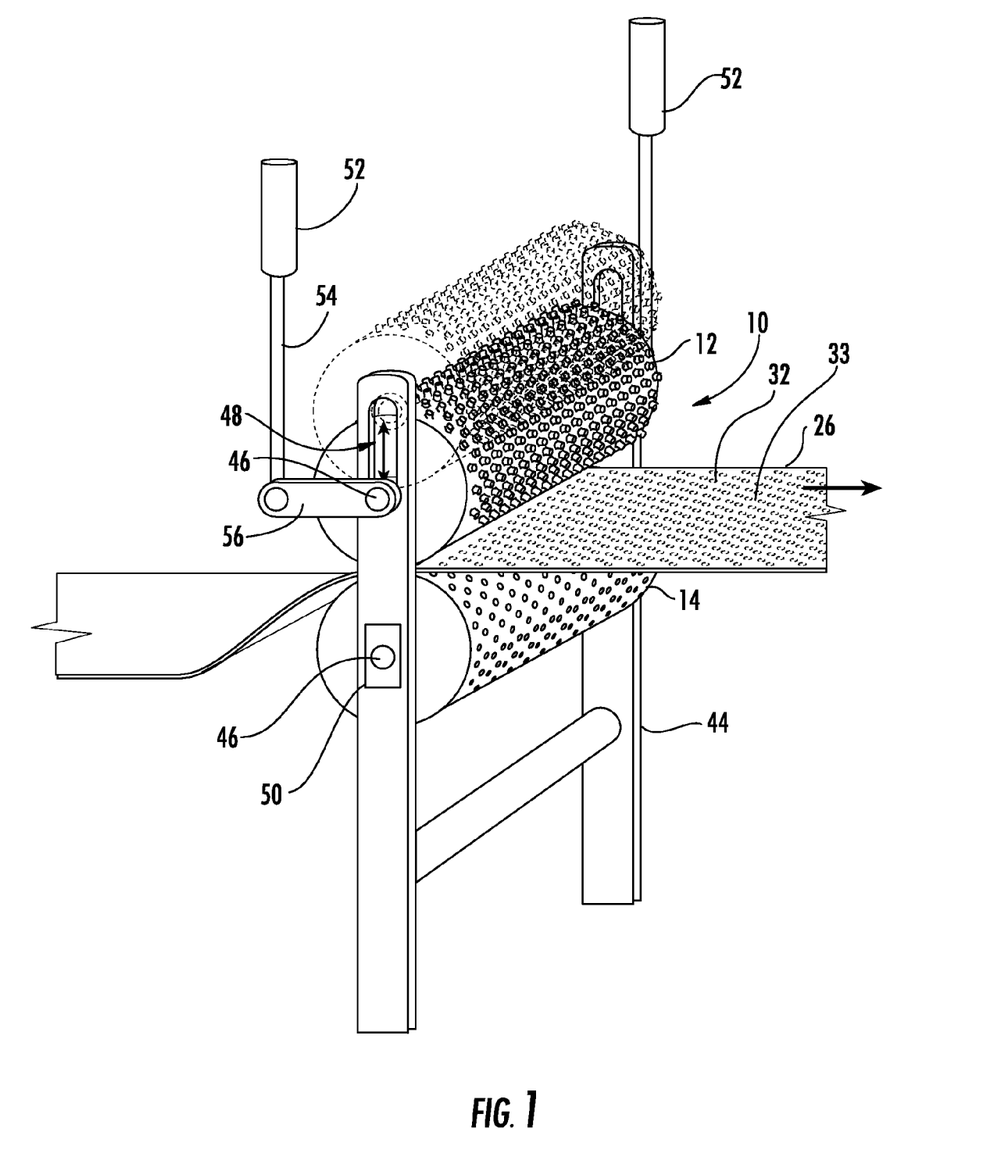
FIG. 1 is a perspective view of a roll assembly comprising a pair of cooperating rolls wherein at least one roll includes a plurality of projections and at least one other roll includes a plurality of corresponding recesses.
Figure 2:
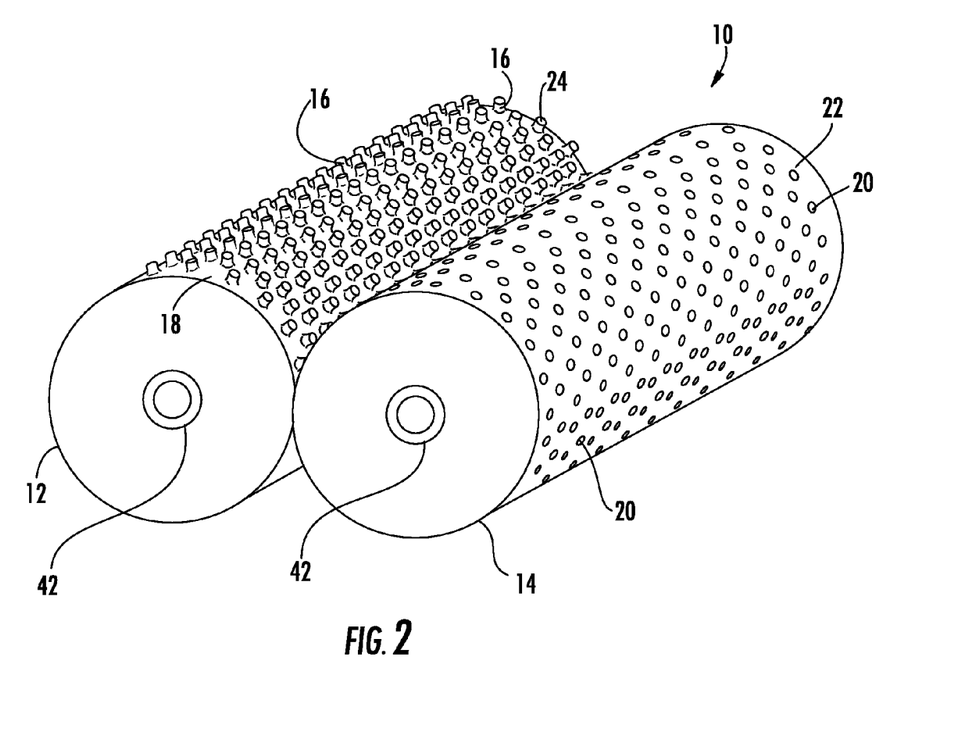
FIG. 2 is an enlarged perspective view of the rolls of FIG. 1.

FIGS. 1 and 2 illustrate a roll assembly, indicated by the reference number 10, for stretching a sheet material. The roll assembly 10 includes a pair of cylindrically shaped rolls 12, 14 that are positioned in a cooperating opposing relationship for receiving a sheet material therebetween. In the illustrated embodiment, the rolls 12, 14 include a plurality of positive projections 16 that extend radially outwardly from a surface 18 of at least one of the rolls, and a plurality of corresponding recesses 20 that are disposed on the surface 22 of the other roll. The recesses 20 are positioned and arranged so as to receive corresponding projections 16 disposed on the opposite roll. When rolls 12, 14 are rotated about their axes, each recess successively becomes aligned opposite a corresponding projection so that each projection at least partially penetrates into the corresponding recess. As a sheet material is directed between the rolls, projections that are in contact with the sheet material each engage a discrete portion of the sheet material. This engagement causes these discrete portions of the sheet material to be pushed into the recesses along with the projections. As a result, these isolated discrete portions of the sheet material are stretched and mechanically elongated. At the same time, areas of the sheet material that surround these stretched and elongated portions are gripped and held by the cooperating opposing surfaces 18, 22 of the rolls 12, 14, resulting in these areas remaining unstretched and unelongated. As can best be seen in FIG. 1, a sheet material 26 is depicted in the process of passing through roll assembly 10. As the sheet material 26 passes between rolls 12, 14, a plurality of discrete island-like portions 32 of the sheet are formed in the sheet. The island-like portions 32 of the sheet material are isolated from adjacent stretched portions of the sheet material by areas of substantially unstretched sheet material 33.

In the embodiment illustrated, the projections 16 are disposed on and project radially outwardly from the cylindrical outer surface 18 of roll 12 and the recesses 20 are formed in the cylindrical outer surface 22 surface of roll 14. However, it should be recognized that the present invention is not limited to this specific position and configuration of the projections and recesses. For example, in some embodiments of the present invention, each roll may include both projections and recesses.

The projections 16, more particularly, have a cylindrical configuration, with a radially outwardly facing outermost surface portion 24 that is positioned for contacting a sheet material as it passes between the pair of cooperating rolls 12, 14. Preferably, the outermost surface portion 24 is somewhat rounded and the junction between the outermost surface portion 24 and the cylindrical side walls of the projection does not present a sharp edge, but instead is rounded or chamfered. In the embodiment illustrated, the recesses 20 are of a frustoconical configuration with inwardly sloping side walls and a flat bottom wall. However, the recesses may have other configurations, such as cylindrical for example. The diameter of the recess opening at the surface 22 of roll 20 is larger than the diameter of the outermost surface portion 24 of the projection and the depth of the recess 20 is greater than the height of the projection 16.

Figures 3A, 3B:
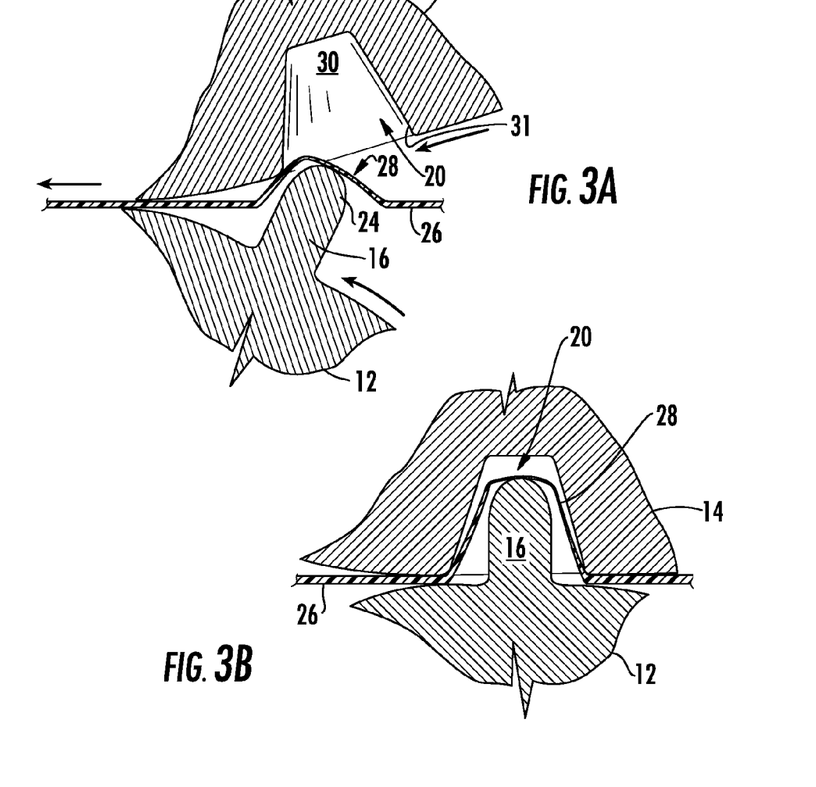
FIGS. 3A-3B illustrate in a step-wise manner a pair of rolls in the process of stretching a sheet material passing therebetween.

FIGS. 3A and 3B illustrate how the outermost surface portion 24 of a projection 16 engages a discrete portion of the sheet material 26 as the rolls 12, 14 rotate and the projection 16 enters the recess 20. As shown in FIG. 3A the projection 16 is just beginning to align with a corresponding recess 20 on the opposite roll 14 as the rolls are rotated. At this point, the projection starts to enter into the recess along with a discrete portion 28 of the sheet material 26. Downstream in the direction of rotation, portions of the sheet material 26 are held between the outer surfaces of rolls 12, 14. As the rolls rotate further, as shown in FIG. 3B, the projection 16 fully enters the recess 20 and the outermost surface portion 24 of the projection engages and pushes the portion 28 of sheet material 26 into the recesses while surrounding portions of the sheet material 26 are gripped between the outer surfaces 18, 22 of rolls 12, 14. This causes stretching and elongation of the discrete portion 28 of the sheet material that is received within the recess while the surrounding portions of the sheet material remain substantially unstretched. The resulting stretched portions of the sheet material are separated and isolated from adjacent stretched portions by substantially unstretched portions of the sheet material. As discussed in greater detail below, the amount of stretching within each discrete portion 28 may be controlled by adjusting the depth to which the projections are permitted to penetrate into the recesses.

Figure 3C:
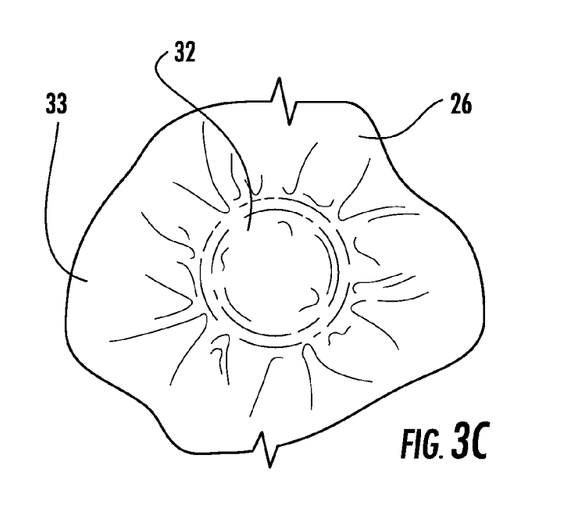
FIG. 3C is a partial illustration of a sheet material that depicts a discrete portion of the sheet material that has been stretched by passing between the pair of rolls of FIGS. 2A and 2B.

The size, shape, and distribution of the recesses may each be configured so that the recesses each have a continuous sidewall 30 that defines an isolated free standing recess for receiving a single projection therein. The recesses may have sidewalls that substantially surround the projection and are unconnected to adjacent recesses. In some embodiments, this may result in the discrete stretched portions having a shape that resembles the cross-sectional shape of the recess and that are separated from adjacent stretched portions. For example, in embodiments where the recess has a circular cross-section, the portion of the sheet material entering the recess will be stretched in all directions (360 degrees about the circumference of the discrete portion) to form a stretched portion on the sheet material having a circular shape. FIG. 3C illustrates a stretched portion 32 of a sheet 26 having a substantially circular shape surrounded by substantially unstretched portions of the sheet material 33.

When used with stretch-activatable composite sheet materials, this stretching process is capable of providing an elastic sheet material with elasticity in all directions. This provides significant improvements in elasticity over composite materials that have been stretch activated by conventional "ring-rolling" techniques where the elasticity is only along one or two directions of the sheet material, i.e. the machine direction or cross machine direction or both.

Figure 4A:
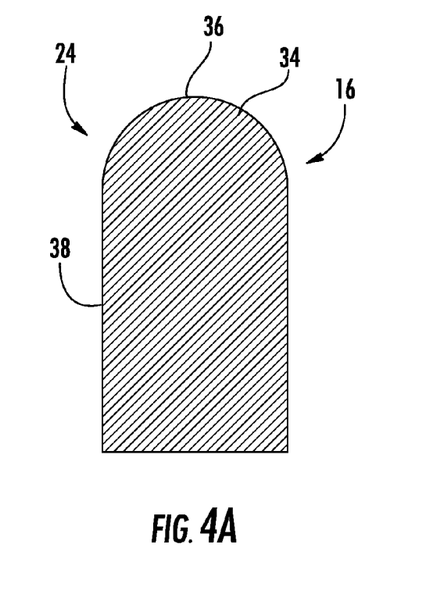
FIGS. 4A-4C illustrate a cross-sectional view of three exemplary projections that can be used in accordance with the invention.
Figure 4B:
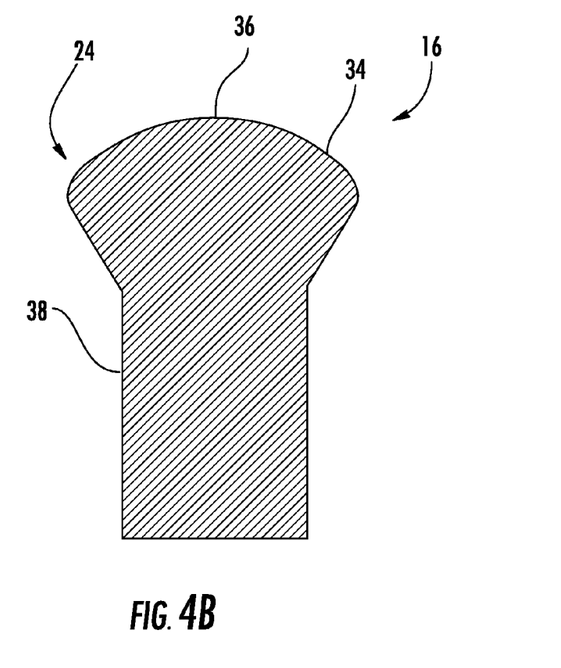
Figure 4C:
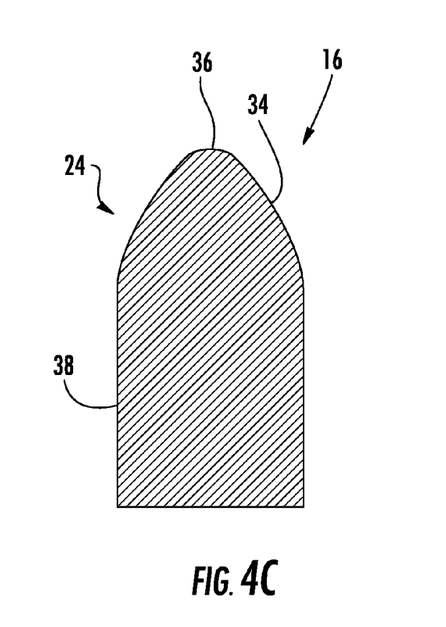

The projections 16 may have a wide variety of shapes and configurations. For example, the projections may have circular, oval, or polygonal cross-sections. The projections may also have a cross-section that varies along the length of the projection. FIGS. 4A through 4C, illustrate three exemplary projections that may be used in accordance with one aspect of the invention. As shown, the projections may comprise a body 38 and an outermost surface portion 24. In the illustrated embodiments, the projections include a generally cylindrical shaft 38 and the outermost surface portion of the projection has a rounded surface 36. As shown in FIG. 4A, the projections may have an outermost surface portion 24 that includes a cap 34 having a semi-spherical shape. In FIG. 4B, a projection is illustrated wherein the outermost surface portion 24 includes a cap 34 having an enlarged "mushroom-like" shape wherein the cross-section of the cap 34 is greater than the cross-section of the body 38. FIG. 4C illustrates a projection having an outermost surface portion that includes a cap 34 having a frusto-conical configuration having a rounded surface 36.

Outermost surface portions having rounded surface areas, such as the semi-spherical, mushroom-shaped, or frusto-conical structures discussed above, may permit greater contact between the rounded surface 36 of the projection and the sheet material. As a result, a greater surface area of the discrete portion of the sheet material can be in direct contact with the projection. This may help improve the ability of the projections to evenly engage and stretch the discrete portions of the sheet material so that uniformity of the stretching within each discrete portion of the sheet material may be improved. The rounded surface areas may also provide activation or stretching in multiple directions within the discrete portion. As discussed above, stretching in multiple directions may provide free standing regions of stretching that are isolated from adjacent free standing regions of stretching. Additionally, the rounded surfaces may help prevent damage to the sheet material, such as tearing, that may otherwise occur in projections having more defined edges.

Referring back to FIG. 4B, a projection having a mushroom-like cap may be particularly useful in the stretching of rubbery sheet materials. Many rubbery materials may have a tendency to stick or adhere to the surfaces of the projections, such as the shaft and the rounded surface. As a result, processing speeds and material requirements may be limited. A projection having a cap comprising a mushroom-like configuration may provide less surface area to which the rubbery sheet material can adhere. As a result, the mushroom-shaped projections may help improve the processability of rubbery materials and may also improve the speeds at which such material can be processed.

Figure 4D:
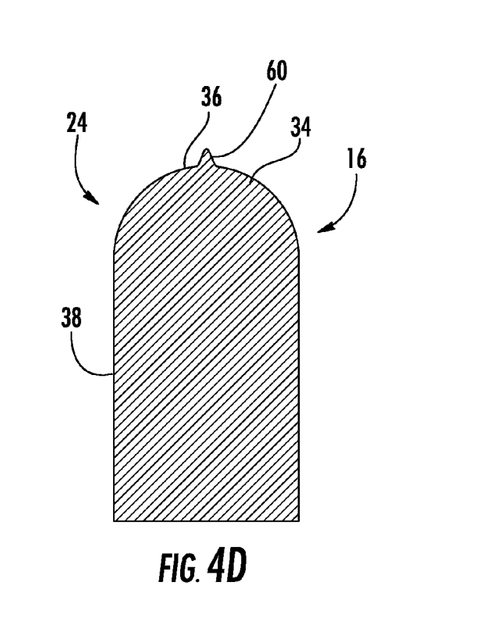
FIG. 4D illustrates a cross-sectional view of a projection having a pin that is configured to create perforations in a sheet material.

In another embodiment, the projections may include a pin that extends outwardly from the rounded surface of the projection and can be used to produce perforations in the sheet material. In this regard, FIG. 4D illustrates a projection 16 that includes a pin 60 extending outwardly from the outermost portion 24 of the projection. In this embodiment, as the projection engages and stretches a discrete portion of the sheet material, the pin causes a perforation to form in the discrete portion of the sheet material. The dimensions of the pin can be selected to produce a perforation having a desired shape and size.

As discussed above, the recesses may be configured to provide a pocket in which the projection can be surrounded by one or more sidewalls. The diameter of the recess with respect to the diameter of the projection can be selected so that there is sufficient space for the discrete portion of the sheet material to be introduced in the clearance that exists between the sidewall of the recess and the projection. For instance, a thicker sheet material may typically require more clearance than a relatively thinner sheet material. Thus, for thicker sheet materials, the diameter of the recesses with respect to the projection is typically be greater than that which is required for a relatively thinner sheet material. In the context of the present invention, the term "diameter" refers to the greatest distance taken across the width of the recess or projection. In one embodiment, the diameter of the recess is about equal to or greater than the diameter of the projection plus 2 times the thickness of the sheet material. Preferably, the recesses may have a diameter that is from about 2 to 85 percent greater than the diameter of the projection. More desirably, the diameter of the recess is from 10 to 50 percent, and in a more specific embodiment, the diameter is about 45 percent greater than the diameter of the corresponding projection. In some embodiments, the projections may have a diameter ranging from about 0.5 to 10 mm and the recesses may have a diameter ranging from about 0.55 to 20 mm.

The size, density and distribution of the projections and corresponding recess can be selected to control the amount of individual stretched portions that may be present within the sheet material. Preferably, the projections are present at a density of from about 15 to 95 percent of the total surface area of the roll. In some embodiments, the projections may be present at a density of from about 25 to 75 percent of the total surface area of the roll. In the context of the present invention, density refers to the surface area of the rolls that includes projections or recesses thereon.

In one embodiment, the density of the projections and recesses across the axial length of the rolls and/or radial circumference (e.g., machine direction) of the rolls may be varied to provide a sheet material having different zones of stretching or activation across the sheet material. As a result, a sheet material that is stretched according to this aspect of the invention may have different zones of stretching in both the machine direction and/or cross direction of the sheet material.

The roll assembly may be driven in a wide variety of ways. For example, in one embodiment, the roll assembly may be product driven so that travel of the sheet material between the pair or rolls causes the rolls to rotate in the machine direction. In other embodiments, the rolls are mounted on central shafts that are rotatably driven by a suitable drive, such as a motor.

In one embodiment, the degree of stretching can be controlled by adjusting the depth to which the projections are permitted to penetrate into the recesses. Referring back to FIG. 1, an arrangement of the roll assembly 10 is illustrated wherein the rolls are disposed on an upright support member 44. Rolls 12, 14 have axially extending shafts 46 that may be connected to a suitable drive mechanism (not shown) so that rolls 12, 14 are rotatably driven. In some embodiments, the rolls may include a bearing, such as an idler bearing, that permit the rolls to rotate about a shaft (see briefly FIG. 2, reference number 42). The support member 44 may also include one or more bearing blocks 50 that rotatably support shafts 46 on the support member.

One or both rolls 12, 14 may be in mechanical communication with one or more devices that are configured to adjust the distance between the rolls. In this regard, FIG. 1 illustrates an embodiment of the roll assembly wherein at least one of the rolls is in mechanical communication with a device for adjusting the distance between the rolls. As shown, two powdered cylinders 52 are mechanically connected to roll 12 via piston 54 and connecting rod 56. The powered cylinders can be used to selectively adjust the distance between rolls 12 and 14. In one embodiment, support member 44 may include channels 48 that permit the position of the rolls with respect to each other to be adjusted. As a result, the distance between the rolls can be adjusted so that the amount of penetration of the projections into the recesses can be controlled. Controlling the distance to which the projections are permitted to penetrate the recesses can be used to control the amount of stretching that occurs within each discrete portion and also control the overall size of the discrete portions of stretched material. The cylinders can be powered in a wide variety of ways including mechanically, pneumatically, electrically, and the like. It should be recognized that in some embodiments the pistons may be directly connected to shaft 46 of roll 12. The distance between the rolls can also be adjusted using other means such as motors, manual adjusting, fluid-pressured devices, and the like.

In yet another embodiment, the invention includes a system for stretching a sheet material comprising two or more roll assemblies that are arranged in series so that the sheet material is successively stretched by each roll assembly in the system. In one embodiment, the projections and recesses on one of the roll assemblies is not registered with the projections and recesses on the other roll assembly. That is, the roll assemblies may be positioned and arranged so that they stretch different regions on the sheet material. In one embodiment, the roll assemblies may be positioned and arranged to provide a sheet material having a plurality of overlapping stretched regions. The degree to which the stretched regions overlap can be controlled to increase or decrease the elastic behavior of the sheet material.

The roll assembly can be used to stretch a wide variety of sheet materials including webs, fabrics, laminates, films, composites, and the like. In one embodiment, the invention may be used to stretch nonwoven sheet materials, such as meltblown, spunbonded, air laid, and carded nonwovens. In one embodiment, the roll assembly can be used to stretch a wide variety of sheet materials. Exemplary sheet materials that can be stretched in accordance with the invention include those described in U.S. Pat. Nos. 6,417,121, 6,417,122, 6,420,285, and 6,506,698 the contents of which are all hereby incorporated by reference in their entirety.

The invention may also be used to mechanically activate composite sheet materials having stretch-activatable elastic properties. For example, the roll assembly may be used to mechanically activate sheet materials such as stretchable laminates, including "zero-strain" stretchable laminates. A "zero-strain" stretch laminate refers to a fabric in which at least two layers of material, one elastic, the other substantially inelastic, are secured to one another along their coextensive surfaces while in a substantially untensioned state. The fabric is subsequently subjected to mechanical stretching, thus permanently elongating the fibers. Exemplary "zero-strain" stretch laminates are discussed in greater detail in U.S. Pat. No. 5,921,973, the contents of which are hereby incorporated by reference in its entirety.

In a further embodiment, the roll assembly may also be used to form an apertured sheet material. For example, U.S. Pat. No. 6,632,504, the contents of which are hereby incorporated by reference in its entirety, describes a nonwoven sheet material comprising a plurality of multicomponent fibers having at least two thermoplastic polymer components arranged in at least first and second separate continuous structured domains. The nonwoven sheet material includes a plurality of frangible bond sites are structured and arranged to readily rupture when the sheet material is passed through the roll assembly. As a result, discrete, spaced-apart apertures can be formed in the free standing stretched regiosns of the sheet material.

In accordance with another embodiment of the invention, the stretched/activated sheet material may comprise a nonwoven fabric having one or more additional layers or components laminated thereto. Exemplary additional layers include continuous or perforated polymer films, films or webs of an elastic polymer, spunbonded nonwoven webs, extensible scrims or nets, an array of extensible or elastic strands, a web of meltblown microfibers, a web of staple fibers, and the like. Where an elastic web or film is used, the composite can be stretch activated by elongation, which causes permanent elongation and stretching of the coherent extensible web of multicomponent fibers, and the resulting composite fabric exhibits elastic properties. Where an extensible nonelastic layer is used, such as polyolefin film for example, the composite can be stretch activated by elongation, for example to at least 20% of its original unstretched length, producing a composite sheet material having excellent softness and drape.

Sheet materials stretched or activated according to the invention may be useful in a variety of applications such as packaging materials, bandaging materials, garments, diapers, training pants, incontinence briefs, supportive clothing, sporting apparel, and personal hygiene products. For example, sheet materials prepared in accordance with the invention can be incorporated into the waist region of a diaper so that fit can be controlled around the wearer's waist. In one embodiment, stretched composite sheet materials prepared in accordance with the invention can have a cloth like hand and good cover characteristics suitable for use in disposable absorbent garments, such as diapers, incontinence pads, sanitary napkins and the like. The composite sheet materials may be particularly useful as components of disposable diapers, such as in leg barrier cuffs, side panels, backsheet, topsheet, and the like.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. An apparatus for stretching a sheet material consisting essentially of:
    a pair of cylindrical rolls positioned in opposed cooperating relation for receiving a sheet material therebetween,
    a plurality of projections on at least one of said rolls, each projection including a body extending radially outwardly and a cap having outermost surface portions positioned for contacting the sheet material, the outermost surface portion of each cap having a semi-spherical shape, wherein the cap has a cross-section that is wider than that of the body such that the projections have a mushroom-like shape, and
    a corresponding plurality of recesses on the other one of said rolls, said recesses being positioned and arranged to receive corresponding projections of said at least one roll, wherein the pair of rolls are configured to stretch the sheet material such that the projections, upon entering the recesses, engage and stretch isolated discrete portions of the sheet material to form a plurality of free standing stretched regions in the sheet material that are separated from each other by substantially unstretched regions.

2. The apparatus of claim 1, including means for rotating the rolls about their cylindrical axes.

3. The apparatus of claim 1, including means for adjusting the depth of penetration of the projections into the recesses to thereby vary the degree of stretching of the sheet material.

4. The apparatus of claim 1, wherein said plurality of projections is present on only one of said rolls and said plurality of recesses is present on only the other one of said rolls.

5. The apparatus of claim 4, wherein the density of the projections on the surface of said roll is from about 15 to 95 percent of the total surface area of the roll.

6. The apparatus of claim 1, wherein said plurality of projections is present on both of said rolls and said corresponding plurality of recesses is also present on both of said rolls.

7. The apparatus of claim 1, wherein each recess is configured to receive only one projection.

8. The apparatus of claim 1, wherein each said projection has a diameter that is from 15 to 98 percent the size of the diameter of the corresponding recess.

9. An apparatus for stretching a sheet material comprising:
a pair of cylindrical rolls positioned in opposed cooperating relation for receiving a sheet material therebetween,
a plurality of projections on at least one of said rolls, each projection including a body extending radially outwardly and a cap having outermost surface portions positioned for contacting the sheet material, the outermost surface portion of each cap having a semi-spherical shape, wherein the cap has a cross-section that is wider than that of the body such that the projections have a mushroom-like shape, and
a corresponding plurality of recesses on the other one of said rolls, said recesses being positioned and arranged to receive corresponding projections of said at least one roll so that the projections, upon entering the recesses, engage and stretch isolated discrete portions of the sheet material to form a plurality of free standing stretched regions in the sheet material that are separated from each other by substantially unstretched regions, and wherein said outermost surface portion includes a pin extending outwardly therefrom that is positioned and arranged to form a perforation in the free standing stretched regions of the sheet material.

10. An apparatus for stretching a sheet material consisting essentially of:
a pair of cylindrical rolls positioned in opposed cooperating relation for receiving a sheet material therebetween,
at least one of said rolls having a cylindrical outer surface and a plurality of projections extending radially outwardly therefrom and having outermost surface portions positioned for contacting the sheet material, the projections having a cross-section defining a mushroom-like shape, and
at least the other one of said rolls having a cylindrical outer surface with a plurality of recesses formed therein, said recesses being positioned and arranged to receive corresponding projections of said at least one roll so that the projections, upon entering the recesses, engage and stretch isolated discrete portions of the sheet material to form a plurality of free standing stretched regions in the sheet material that are separated from each other by substantially unstretched regions.

11. The apparatus of claim 10, including means for rotating the rolls about their cylindrical axes.

12. The apparatus of claim 10, including means for adjusting the depth of penetration of the projections into the recesses to thereby vary the degree of stretching of the sheet material.

13. The apparatus of claim 10, wherein said plurality of projections is present on only one of said rolls and said plurality of recesses is present on only the other one of said rolls.

14. A system for stretching a sheet material consisting essentially of:
at least one pair of cylindrical rolls positioned in opposed cooperating relation for receiving a sheet material therebetween,
a plurality of projections on at least one of said rolls extending radially outwardly and having a cross-section defining a mushroom-like shape and being positioned for contacting the sheet material,
a corresponding plurality of recesses on the other one of said rolls, said recesses being positioned and arranged to receive corresponding projections of said at least one roll so that the projections, upon entering the recesses, engage and stretch isolated discrete portions of the sheet material to form a plurality of free standing stretched regions in the sheet material that are separated from each other by substantially unstretched regions, and
at least one powered cylinder being operatively connected to one of said rolls and being configured to adjust the distance between said pair of rolls.

15. The system according to claim 14, wherein the system comprises a first pair of said cylindrical rolls and a second pair of said cylindrical rolls, and wherein the first and second pairs of cylindrical rolls are positioned and arranged to form a plurality of overlapping stretched regions in the sheet material.

\* \* \* \* \*